United States Patent [19]

Sherry et al.

[11] Patent Number: 5,630,997
[45] Date of Patent: May 20, 1997

[54] PHOSPHORYLATED POLYAZAMACROCYCLIC COMPOUNDS FOR COMPLEXATION OF METAL IONS

[75] Inventors: A. Dean Sherry, Dallas; Garry E. Kiefer, Lake Jackson, both of Tex.

[73] Assignees: Board of Regents, The University of Texas System, Austin, Tex.; Dow Chemical Company, Midland, Mich.

[21] Appl. No.: 336,180

[22] Filed: Nov. 8, 1994

Related U.S. Application Data

[60] Division of Ser. No. 923,715, Jul. 31, 1992, Pat. No. 5,362,476, which is a continuation-in-part of Ser. No. 615,619, Nov. 19, 1990, Pat. No. 5,342,606, which is a continuation-in-part of Ser. No. 357,193, May 25, 1989, abandoned, and Ser. No. 291,053, Dec. 28, 1988, Pat. No. 4,983,376, which is a continuation-in-part of Ser. No. 7,729, Jan. 27, 1987, abandoned, which is a continuation-in-part of Ser. No. 662,075, Oct. 18, 1984, Pat. No. 4,639,365.

[51] Int. Cl.$^6$ ................................ A61B 5/055
[52] U.S. Cl. ............ 424/9.363; 540/465; 540/474; 514/79; 514/836; 534/15; 436/173
[58] Field of Search .................... 424/9.363; 540/465, 540/474; 514/79, 836; 436/173; 128/653.4, 654; 534/15

[56] References Cited

U.S. PATENT DOCUMENTS

| | | | |
|---|---|---|---|
| 4,352,751 | 10/1982 | Wieder | 260/112 R |
| 4,472,509 | 9/1984 | Gansow | 436/548 |
| 4,639,365 | 1/1987 | Sherry | 424/9 |
| 4,647,447 | 3/1987 | Gries et al. | 424/9 |
| 4,731,239 | 3/1988 | Gordon | 424/9 |
| 4,735,796 | 4/1988 | Gordon | 424/9 |
| 4,775,522 | 10/1988 | Clark, Jr. | 424/9 |
| 4,957,939 | 9/1990 | Gries et al. | 424/9 |
| 4,963,344 | 10/1990 | Gries et al. | 424/9 |
| 4,983,376 | 1/1991 | Sherry | 424/9 |
| 5,236,695 | 8/1993 | Winchell et al. | 424/9 |

FOREIGN PATENT DOCUMENTS

0404605  12/1990  European Pat. Off.

OTHER PUBLICATIONS

Kabachnik, MI, *Izv. Akad. Nauk. SSSR, Ser. Khim.*, (1984) pp. 769–777.

Desreux, *Inorganic Chemistry* 19:1319–1324 (1980).

Geraldes et al., *Inorganic Chemistry* 24(23):3876 (1985).

Geraldes et al. *Magnetic Resonance in Medicine*, 3:242–250 (1986).

Sherry et al., *J. Magnetic Resonance*, 66:511–524 (1986).

*Primary Examiner*—Gary E. Hollinden
*Attorney, Agent, or Firm*—Arnold, White & Durkee

[57] ABSTRACT

The present invention relates to a new polyazamacrocyclic compound or a salt thereof and its uses as a tissue specific chelator. The compound has the formula

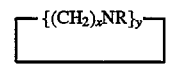

where
x is 2, 3 or a combination of p 2(s) and q 3(s) where p +q=y;
y is 3 or 4;
R is $(CH_2)_zP(=O)OR^1OR^2$;
$R^1$ is H or $CH_3$;
$R^2$ is $C_nH_{1+2n}$;
n is 4 to 6;
z is 1 to 3.

In one important embodiment, this compound may be complexed with a metal to be a polyazamacrocyclic compound-metal complex having the formula

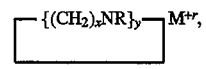

where
r is 2 or 3; and
M is a metal ion, including a lanthanide, a heavy metal, or a radionuclide metal.

27 Claims, 2 Drawing Sheets

PHOSPHORYLATED POLYAZAMACROCYCLIC COMPOUNDS FOR COMPLEXATION OF METAL IONS

This is a divisional of application Ser. No. 07/923,715 filed Jul. 31, 1992 and issued Nov. 8, 1994 as U.S. Pat. No. 5,362,476 which is a continuation-in-part of U.S. Ser. No. 07/615,619 filed Nov. 19, 1990, issued as U.S. Pat. No. 5,342,60 which is a continuation-in-part of U.S. Ser. No. 07/357,193 filed May 25, 1989 now abandoned, and U.S. Ser. No. 07/291,053 filed Dec.28, 1988, the latter now issued as U.S. Pat. No. 4,983,376 which is a continuation-in-part of application Ser. No. 07/007,729 filed on Jan. 27, 1987, (abandoned) which was a continuation-in-part of application Ser. No. 06/662,075, filed on Oct. 18, 1984, now issued as U.S. Pat. No. 4,639,365. All of the above applications are incorporated by reference herein.

BACKGROUND OF THE INVENTION

1. Field of the Invention

The present invention relates to compositions and methods for enhancing contrast in imaging internal structures and functions of living subjects.

2. Imaging Modalities

Imaging of internal structures and functions of living subjects may be accomplished by applying electromagnetic radiation from external sources (as in conventional x-rays and computerized axial tomography) or internal sources (as in PET or positron emission tomography and radionuclide scans). Use of ionizing radiation is avoided in imaging with nuclear magnetic resonance (NMR) and untrasonography, making these methods advantageous for many applications.

Whatever the imaging modality, consideration is given to means of increasing image contrast through localization of contrast agents in the region to be imaged. Such agents are frequently metals which emit, absorb, or scatter energy or, as in the case with NMR agents, increase the image signal strength locally. For best effect, agents must be localized. This may be accomplished, for example, by direct injection of contrast agent (as in myelograms or retrograde urethrograms), through metabolic uptake of an agent (as in PET), and by conjugation of contrast agents with monoclonal antibodies which tend to accumulate in certain tissues. The latter process in particular has been used in NMR image enhancement with chelated metal ions. Though well known, the process has several shortcomings:

1 preparation of the antibody is complex;
2 diminished immunoreactivity of the antibody occurs following conjugation;
3 there is limited uptake of the conjugate by the target tissue; and
4 there may be unfavorable interactions between the chelated ion and the antibody.

Because of the advantages of NMR imaging (good resolution and avoidance of ionizing radiation), an NMR contrast agent capable of greater localization would be clinically important. Such an agent would offer significant advantages over contrast agents of the prior art.

3. NMR Contrast Agents

The quality of the images obtained from an NMR scan is based on two properties: the proton densities of the various tissues and differences in proton relaxation rates. The proton density of tissues cannot be readily altered. Proton relaxation rates can be adjusted by adding a paramagnetic relaxation agent, more commonly known as a "contrast agent." Contrast agents enhance the contrast in NMR images between magnetically similar but histologically dissimilar tissues.

Gadolinium, which has strong paramagnetic properties because of its seven unpaired electrons, has been tested as a contrast agent. It has a large magnetic moment which efficiently relaxes magnetic nuclei and increases tissue contrast in the region of the gadolinium.

One drawback of gadolinium as a contrast agent is its toxicity to animals, although a possible remedy for this problem is incorporation of gadolinium in a compound that would pass through the body and be excreted without releasing toxic gadolinium ions. Unfortunately, the rare earth elements (including gadolinium) do not form stable covalent bonds with organic molecules, so such molecules can decompose in vivo and release the toxic ions.

Thus, there is a need for effective contrast agents which avoid the toxicity problems inherent in using gadolinium or another metal ion. Further, it is desirable that a contrast agent control or influence the distribution of chelated ions in the body.

A even more desirable approach to the site-specific delivery of metal ions would be through use of stable chelates having inherent affinity for various tissue types. Inherent tissue affinity built into the organic chelating agent through modifications in both ionic charge and degree of lipophilic character would offer substantial advantages over currently available agents.

SUMMARY OF THE INVENTION

The present invention relates to a series of new phosphorous-containing triaza- and tetraazamacrocyclic chelators which have inherent affinity for certain tissues. Following intravascular injection, chelates comprising these compositions preferentially accumulate in certain tissues, depending on the time after injection. In particular, 1,4,7,10 tetraazacyclododecane-1,4,7,10-tetra (methylenephosphonate monobutyl ester) has a high affinity for liver tissue and the gastrointestinal tract (in that order). Chelates comprising this agent are thus suitable for liver imaging because of the lipophilic character imparted by the ester functionality. Such agents are not metabolized, and eventually pass out of the body via the urine or feces.

While the monobutyl ester above appears well adapted for liver imaging, analogous alkyl esters have also been considered. Monopentyl esters are nearly as good for liver imaging, but monooctyl esters have the disadvantage of very low aqueous solubility. Monopropyl esters, on the other hand, may be used for liver imaging but are less efficient because a substantial portion of the agent is rapidly lost to the kidneys; monoisopropyl esters would behave similarly. Hence, the most preferred embodiment is that described above with monobutyl esters.

For use with NMR, compositions of the present invention must be chelated with a metallic element. While the element is preferably of the rare-earth series (preferably gadolinium), those skilled in the art will recognize that other metallic ions might also be useful for imaging. For example, other metal chelates (e.g., chelates of radionuclides or heavy metals) may be used for imaging by scintigraphy, x-radiation, and analogous imaging methods where changes in local tissue parameters can increase image contrast. Depending on the metal ion preferred for a particular contrast agent application, either triaza- or tetraaza- compounds of the present invention may be selected as chelators.

Chelators of the present invention have the formula

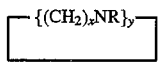

where
x is 2, 3 or a combination of p 2(s) and q 3(s) where p+q=y;
y is 3 or 4;
R is $(CH_2)_zP(=O)OR^1OR^2$;
$R^1$ is H or $CH_3$;
$R^2$ is butyl, pentyl or hexyl; and
z is 1 to 3.

In one important embodiment, this compound may be complexed with a metal to be a polyazamacrocyclic compound-metal complex having the formula

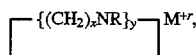

where
x is 2, 3 or a combination of p 2(s) and q 3(s) where p+q=y;
y is 3 or 4;
R is $(CH_2)_zP(=O)OR^1OR^2$;
$R^1$ is H or $CH_3$;
$R^2$ is butyl, pentyl or hexyl;
z is 1 to 3;
r is 2 or 3; and
M is a metal ion.

The y designation characterizes the compound as triazamacrocyclic or tetraazamacrocyclic. The x is preferably 2, although 3 is feasible under many circumstances. Combinations of p 2(s) and q 3(s) for x are of course readily produced but the total of p+q must be y for the number of units in the polyaza macrocycle. H or $CH_3$ for $R^1$ are believed equivalent in use.

In a preferred embodiment of either the compound or its metal complex y is 3, p is 1 and q is 2 or p is 2 and q is 1.

In another preferred embodiment of the compound or its metal complex, y is 4, p is 1 and q is 3, p is 2 and q is 2 or p is 3 and q is 1 and z is most preferably 1. n is preferably 2.

In a more preferred embodiment x is 2, y is 4, z is 1, $R^1$ is H and $R^2$ is butyl.

In another preferred embodiment X is 2, y is 3, z is 1, $R^1$ is H and $R^2$ is butyl.

The $M^{+r}$ is preferably a paramagnetic lanthanide, although other divalent or trivalent metal ions, including radionuclides and heavy metals, may also be so complexed.

In one important application, the present invention involves a method for enhancing a magnetic resonance image of a subject. This method comprises administering to the subject a polyazamacrocyclic compound-metal complex having the formula

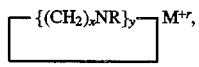

where
x is 2, 3 or a combination of p 2(s) and q 3(s) where p+q=y;
y is 3 or 4;
R is $(CH_2)_zP(=O)OR^1OR^2$;
$R^1$ is H or $CH_3$;
$R^2$ is butyl, pentyl or hexyl;
z is 1 to 3;
r is 3; and
M is gadolinium.

DETAILED DESCRIPTION OF PREFERRED EMBODIMENTS

EXAMPLE 1

Triazamacrocyclic Compounds

NOTPME Synthesis

Materials 1,4,7-triazacyclononane, paraformaldehyde, diethylphosphite, and activated carbon Darco G-60 were purchased from Aldrich Chemical Company. $MgSO_4$ was from Mallickrodt, sodium hydroxide, and benzene from J. T. Baker, and diethylether from Fisher Scientific. All chemicals were of highest purity and were used without further purification. Solutions of $ZnCl_2$, $GdCl_2$, $MgCl_2$ and $CaCl_2$ were standardized complexometrically.

Figure 1:
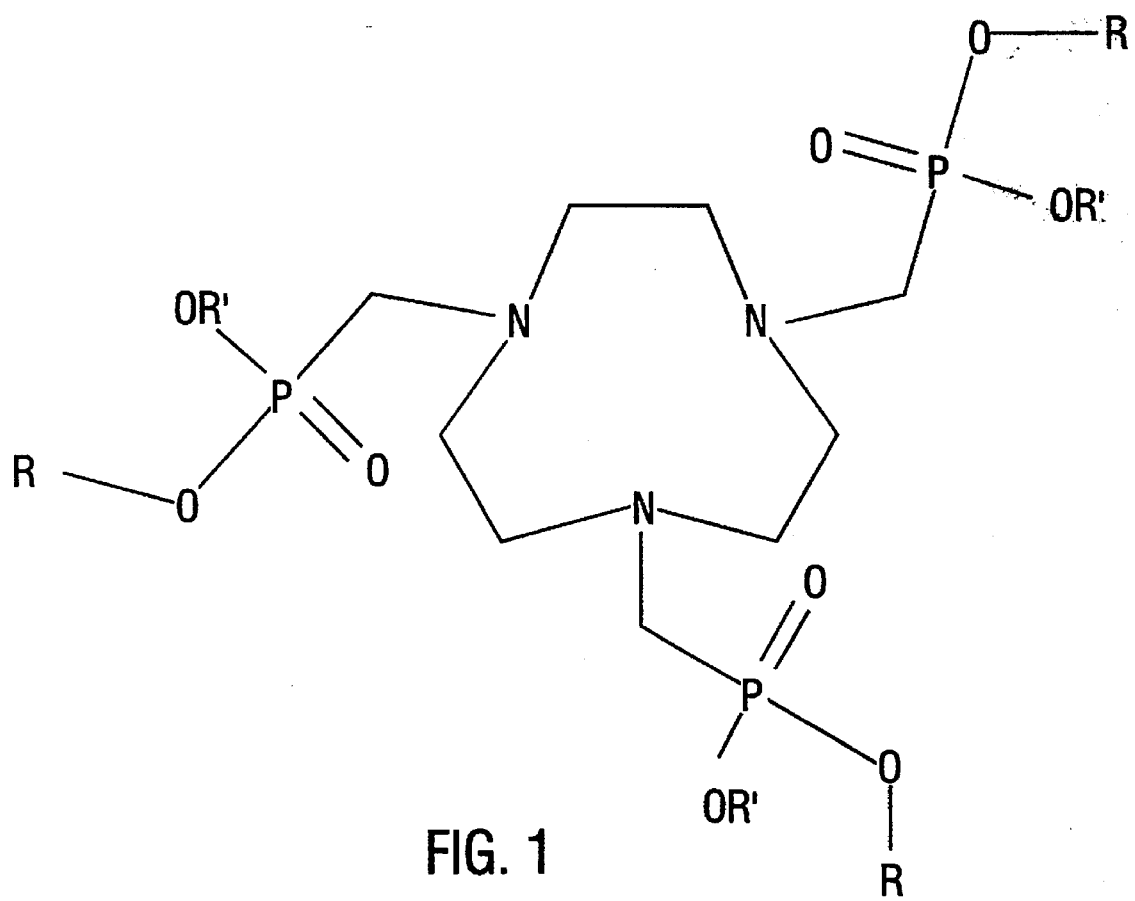
FIG. 1 schematically illustrates the structure of NOTPME (where R is $CH_2CH_3$ and $R^1$ is H).

Synthesis of NOTPME 1,4,7-Triazacyclononane (1.91 g, 14.71 mmol) and diethylphosphite (7.018 g, 16.94 mmol, 15% excess) were dissolved in 125 ml of benzene and heated to reflux. Anhydrous paraformaldehyde (1.727 g, 30% excess) was added in small portions to the above refluxing mixture while the benzene-water azeotropic mixture was removed by distillation. After the addition of paraformaldehyde was complete, the entire solution was boiled for 30 minutes and then evaporated to obtain a yellow viscous oil. The oil was dissolved in 150 ml anhydrous diethylether and dried with anhydrous $MgSO_4$ overnight. $MgSO_4$, along with a white precipitate which formed, were filtered off and discarded. The filtrate was decolorized with activated carbon and filtered. The filtrate was evaporated in vacuum to obtain a viscous oil of 1,4,7-triazacyclononane-N,N',N"-tris(methylenephosphonate diethylester) (NOTPDE). Pure NOTPDE was obtained in 96% yield (9.21 g, 14.17 mmol) and was used for the synthesis of NOTPME (structure shown in FIG. 1) without further purification. $^1H$ NMR data of NOTPDE in $CDCl_3$ (TMS at zero) are as follows: δ (ppm) : 1.33 (t, 18H, —$CH_3$), 2.97 (s, 12H, N—$CH_2$), 3.00 (d, 6H, P—$CH_2$), 4.13 (p, 12H, O—$CH_2$).

9.20 g of NOTPDE (14.15 mmol) was mixed with 2.50 g of NaOH in 9 ml $H_2O$) and after 2 hours the entire reaction mixture was boiled until a clear solution was obtained (approximately 5 minutes). The solution was cooled to room temperature and was allowed to stand overnight. The crystals formed were filtered off from the viscous mother liquor using a pressure filter funnel with a coarse porosity grade filter disc. The crystals were washed once with cold absolute ethanol, three times with absolute ethanol-diethylether (1:1) mixture and finally with diethyl ether. The crystals of Na$_3$NOTPME were dried in dry nitrogen stream at 25° C. for 2 hours. Traces of H$_2$O and ethanol were removed upon vacuum drying (10 mm Hg) NOTPME for 5 hours at 50° C. Pure NOTPME thus obtained were white crystals, very hygroscopic, readily soluble in H$_2$O and fairly soluble in chloroform. The yield of pure NOTPME was 40.8% (3.24 g, 5.77 mmol).

$^1$H NMR (D$_2$O, HDO peak set as reference at 4.90 ppm), δ (ppm): 1.23 (t, 9H, —CH$_3$), 2.54 (s, broad, 6H, P—CH$_2$), 2.79 (s, broad, 12 H, N—CH$_2$), 3.91 (p, 6H, O—CH$_2$).

EXAMPLE 2

Tetraazamacrocyclic Compounds

DOTEP Synthesis

Figure 2:
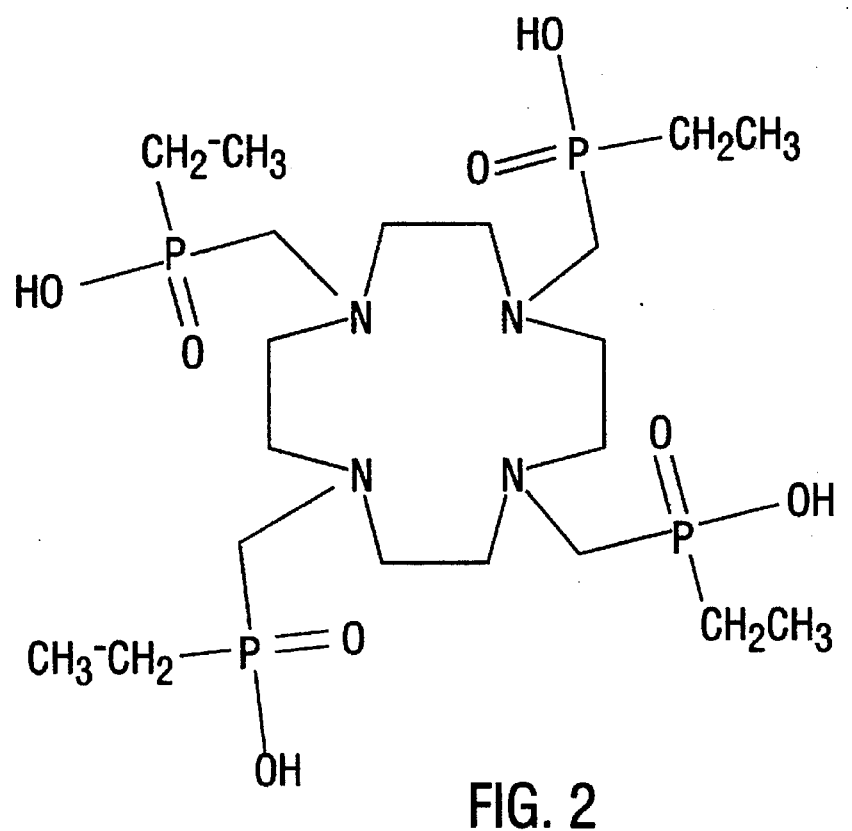
FIG. 2 schematically illustrates the structure of DOTEP.

DOTEP, shown in FIG. 2, was prepared as follows. 2 ml of dichloroethylphosphine was slowly mixed with ice to form the corresponding ethylphosphinic acid. After warming to room temperature, 390 mg of 1,4,7,10-tetraazacyclododecane tetrahydrochloride (cyclen.4HCl) (Parrish Chem. Co., Ogden, Utah) was added and the mixture heated to boiling under a nitrogen atmosphere. A solution containing 157 mg of paraformaldehyde dissolved in 10 ml of 6M HCl was added at a rate of 0.5 ml/hr, while the mixture continued to reflux. The final mixture was refluxed an additional 4 hours then cooled to room temperature. This solution was concentrated under vacuum to a viscous oil, redissolved into 6 ml of water and loaded onto a DOWEX 50Wx4 (hydrogen form) cation exchange column (7.5 ml bed volume). The column was washed to neutrality with water and the product eluted with 60 ml of 0.66 M HCl. The fractions containing DOTEP were combined, evaporated, redissolved in absolute ethanol and evaporated to a white solid. This solid was dispersed into anhydrous ether, filtered off, pre-dried under nitrogen and dried under vacuum at 60°–70°C. to yield a white, very hygroscopic solid (360 mg, 44% yield). This solid was stored in sealed ampoules. Elemental analysis and potentiometry shows the solid to be DOTEP.2HCl.

EXAMPLE 3

Tetraazamacrocyclic Compounds

DOTP Dibutyl Ester Synthesis

Tetraaza-12-crown-4 4HCl (1 g, 3.14×10$^{-3}$ mol) was dissolved in water and the pH adjusted to 9.0 using 1M NaOH. The solvent was evaporated and the residue dried under vacuum for 1 hour. Formaldehyde (6.6 mL of 37% solution, 7.15 g, 0.24 mol) was added and the solution stirred for 30 minutes at room temperature. Dibutyl phosphite (5.10 mL of 96% purity, 0.025 mol) was then added and the reaction mixture stirred for 15 hours at room temperature (dipentyl and dihexyl phosphite are so used to produce dipentyl and dihexyl esters respectively). The resulting mixture consisted of two layers. The bottom layer was mostly excess formaldehyde, as indicated by $^{13}$C NMR. The upper layer contained the product and excess phosphite. This layer was separated, concentrated and dried under vacuum for 1 hour. The resulting syrup was loaded onto a silica-gel column (2.5×11 cm). The excess phosphite was washed away with methylene chloride (250 mL). The product was eluted with 5% methanol in methylene chloride. 20 mL fractions were collected and monitored by TLC. The fractions containing the product were combined, concentrated, and dried under vacuum,. A pale yellow oil was obtained in 75% yield (2.34 g) . $^1$H NMR (CDCl$_3$): 0.87 (t, J=7.3, 6H), 1.33 (m, J=7.3, 4H), 1.60 (p, J=7.3, 4H), 3.18 (br s, 4H), 3.39 (d, J=8.5, 2H), 4.03 (m, J=7.3, 6.1, 4H). $^{13}$C NMR (CDCl$_3$): 11.3 (s), 16.5 (s), 30.3 (d, J=5.9), 47.3 (d, J=148), 50.0 (br s), 63.8 (d, J=7.3).

EXAMPLE 4

Tetraazamacrocyclic Compounds

DOTP Monobutyl Ester (DOTPMB) Synthesis

The dibutyl ester was suspended in 1M KOH (20 mL). The mixture was stirred at 85° C. for 17 hours and then at 106° C. for 9 hours. The solvent was evaporated and the sample dried under vacuum for 1 hour. Methylene chloride (40 mL) was then added and the remaining solid KOH crushed as much as possible. The solvent was again evaporated and this procedure repeated another two times. The solvent was evaporated and the residue dissolved in methanol (60 mL). The mixture was filtered and then concentrated to a syrup under vacuum. Methylene chloride (80 mL) was added and the mixture filtered. The solvent was evaporated and the residue dried under vacuum to yield a white solid in 71% yield. $^{13}$C NMR (D$_2$O; ref. dioxane at 67.0 ppm): 13.5, 18.9, 32.9 (d, J=5.9), 50.7 (d, J=140.6), 51.5 (br s), 64.6 (d, J=5.9).

EXAMPLE 5

Biodistribution of Gd-DOTPMB

Complexation and Biodistribution

Figure 3:
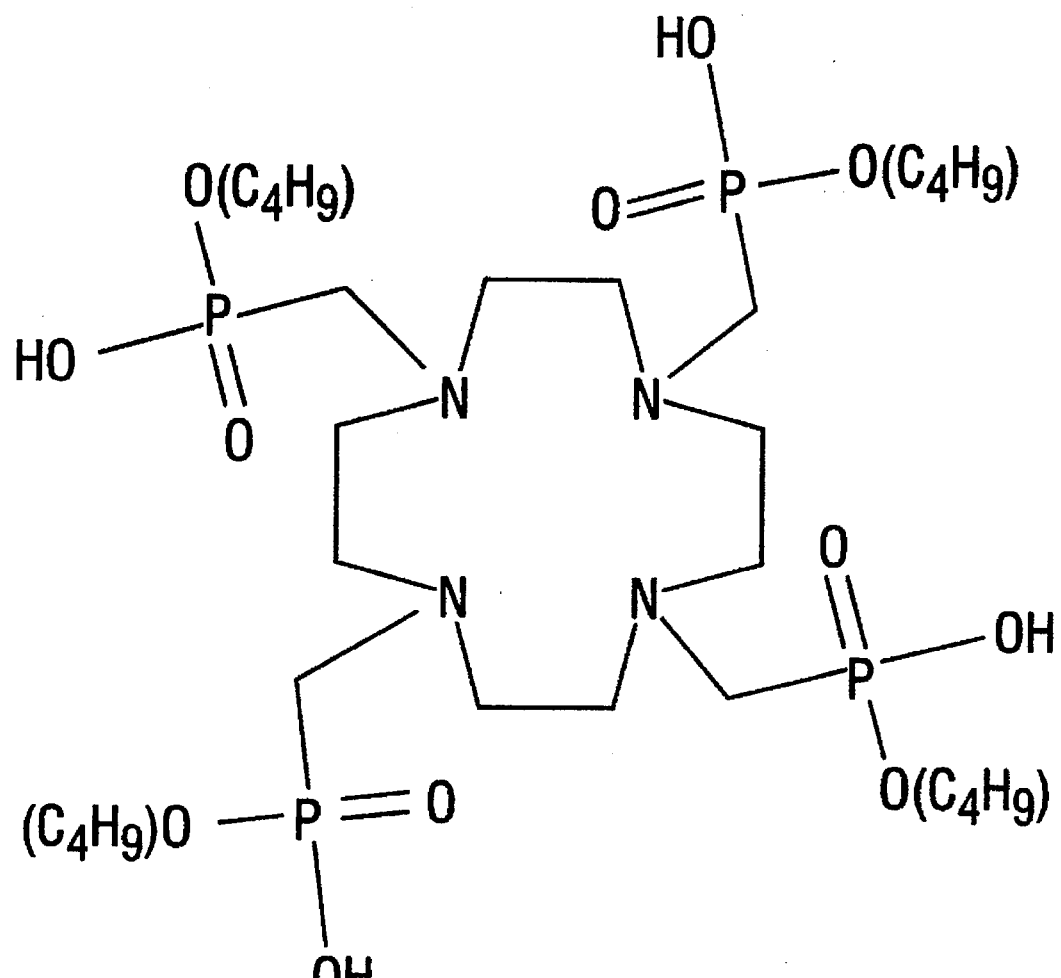
FIG. 3 schematically illustrates the structure of DOTPMB.

A complex of DOTPMB (FIG. 3) and Gd (0.012 M based on metal, 2:1 ligand/metal ratio) was prepared and spiked with tracer quantities of Gd-159. Complexation was determined to be greater than 99% by standard analytical methods described in earlier reports. Two Sprague-Dawley rats were then injected with the complex at a 0.05 mmol/kg level. The animals were sacrificed after 30 minutes and dissected for biodistribution data (Tables I and II); actual counts obtained from various tissues are shown in Table II. At the end of this time period, an average of 58% of the injected dose was found in small intestine (see entry for SM INTES in Table I). A similar experiment performed with a third rat yielded 52% in small intestine (Tables III and IV); actual counts obtained from various tissues are shown in Table IV. The bulk of the remaining activity in each case was eliminated via the renal system (Tables II and IV).

In order for localization to occur in the small intestine, the complex must first pass through the liver. Thus, since liver activity at the 30 minute time point (1%) was minimal (see e.g., Table I), the peak of liver localization passed within the prior 30 minutes. This is evident in an example of biodistribution 15 minutes after administration of chelated tracer, which is documented in Tables VIII and IX. Although by 15 minutes the peak of liver localization had passed for mouse 1, with 4% in the liver and 88% in the small intestine, mouse 2 still had a significant liver concentration (66%) at the 15 minute point. These animal models suggest that imaging within 15 minutes after administration of chelated tracer will be necessary for best definition of the liver. The following test description supports that conclusion. Higher doses would, of course, lengthen the time of liver localization at concentrations sufficient to substantially enhance liver imaging.

Gamma Imaging of DOTPMB

A Sm(153)-DOTPMB complex was prepared as described above for gamma imaging of a Sprague-Dawley rat. Images were acquired at one minute intervals over a 16-minute period. The image sequence revealed concentration of the chelate in liver within one minute following injection. The complex is then rapidly transported from the liver to the stomach and small intestine. Tables V, VI and VII contain data taken at 1 hour, 24 hours and 72 hours after injection, showing movement of the agent from stomach and intestine to feces.

TABLE I

TIME: 30 Minute Biodistribution
DATE    LIGAND          METAL       COMMENTS
8/6/91  DOTPMB-K,       Gd-159,     99% Complexation
4:1, LIG:MET Molar Ratio, (Metal = 3 × 10−4M)

% DOSE/GRAM

|  | RAT 1 | RAT 2 | AVERAGE | +/− |
|---|---|---|---|---|
| WEIGHT | 216.72 | 228.17 | 222.45 | 8.096 |
| BONE | 0.019 | 0.006 | 0.01 | 0.009 |
| TAIL | 0.077 | 0.068 | 0.07 | 0.007 |
| LIVER | 0.114 | 0.069 | 0.09 | 0.032 |
| KIDNEY | 0.169 | 0.126 | 0.15 | 0.031 |
| SPLEEN | 0.011 | 0.021 | 0.02 | 0.007 |
| MUSCLE | 0.007 | 0.005 | 0.01 | 0.001 |
| BLOOD | 0.021 | 0.017 | 0.02 | 0.003 |
| HEART | 0.014 | 0.000 | 0.01 | 0.010 |
| LUNG | 0.126 | 0.023 | 0.07 | 0.073 |
| BRAIN | 0.002 | 0.003 | 0.00 | 0.000 |

0.000 = NO ACTIVITY DETECTED

DOSE

| BONE | 0.281 | 0.106 | 0.193 | 0.124 |
|---|---|---|---|---|
| TAIL | 0.212 | 0.191 | 0.201 | 0.015 |
| LIVER | 1.234 | 0.755 | 0.994 | 0.339 |
| KIDNEY | 0.392 | 0.299 | 0.346 | 0.066 |

TABLE I-continued

| SPLEEN | 0.009 | 0.011 | 0.010 | 0.002 |
|---|---|---|---|---|
| MUSCLE | 0.658 | 0.506 | 0.582 | 0.108 |
| BLOOD | 0.299 | 0.250 | 0.274 | 0.035 |
| HEART | 0.011 | 0.000 | 0.006 | 0.008 |
| LUNG | 0.158 | 0.029 | 0.094 | 0.091 |
| BRAIN | 0.004 | 0.004 | 0.004 | 0.001 |
| STOMACH | 0.574 | 0.530 | 0.552 | 0.031 |
| SM INTES | 80.304 | 36.405 | 58.354 | 31.041 |
| LG INTES | 0.591 | 0.433 | 0.512 | 0.112 |

TABLE II (see legend for Table I)

| DATA | COUNTS | ORGAN | N ENTER WT | BCKG COR | % DOSE/G | % DOSE |
|---|---|---|---|---|---|---|
| 1 |  | Std A | × Rat 1 Wt | 0 |  |  |
| 1 |  | Std B | × 216.72 | 0 |  |  |
| 2 | 414838 | Std C | av 414404.5 | 414405 |  |  |
| 3 | 1480 | Bone | 0.60 | 47 | 1.87E−02 | 2.81E−01 |
| 4 | 1311 | Tail | 2.74 | 878 | 7.73E−02 | 2.12E−01 |
| 5 | 5546 | Liver | 10.86 | 5113 | 1.14E−01 | 1.23E+00 |
| 6 | 2058 | Kidney | 2.32 | 1625 | 1.69E−01 | 3.92E−01 |
| 7 | 469 | Spleen | 0.75 | 36 | 1.14E−02 | 8.57E−01 |
| 8 | 478 | Muscle | 1.52 | 45 | 7.06E−03 | 6.58E−01 |
| 9 | 576 | Blood | 1.62 | 143 | 2.12E−02 | 2.99E−01 |
| 10 | 481 | Heart | 0.82 | 48 | 1.40E−02 | 1.15E−02 |
| 11 | 1088 | Lung | 1.25 | 655 | 1.26E−01 | 1.58E−01 |
| 12 | 449 | Brain | 1.62 | 16 | 2.31E−03 | 3.74E−03 |
| 13 | 2811 | Stomach |  | 2378 | 5.74E−01 |  |
| 14 | 333215 | Sm Intes |  | 332782 | 8.03E+01 |  |
| 15 | 2883 | Lg Intes |  | 2450 | 5.91E−01 |  |
| 16 | 150310 | Urine |  | 149877 | 3.62E+01 |  |
| 17 | 400 | Urine |  | 0 | 0.00E+00 |  |
| 18 | 428 | Urine |  | 0 | 0.00E+00 |  |
| 19 | 443 | BKG | 228.17 | WT Rat 2 |  |  |
| 20 | 451 | Bone | 0.67 | 18 | 6.30E−03 | 1.06E−01 |
| 21 | 1225 | Tail | 2.82 | 792 | 6.77E−02 | 1.91E−01 |
| 22 | 3561 | Liver | 10.96 | 3128 | 6.89E−02 | 7.55E−01 |
| 23 | 1674 | Kidney | 2.38 | 1241 | 1.26E−01 | 2.99E−01 |
| 24 | 480 | Spleen | 0.53 | 47 | 2.12E0−02 | 1.12E−02 |
| 25 | 469 | Muscle | 1.66 | 36 | 5.16E−03 | 5.06E−01 |
| 26 | 559 | Blood | 1.80 | 126 | 1.68E−02 | 2.50E−01 |
| 27 | 430 | Heart | 0.85 | 0 | 0.00E+00 | 0.00E+00 |
| 28 | 554 | Lung | 1.28 | 121 | 2.27E−02 | 2.91E−02 |
| 29 | 452 | Brain | 1.55 | 19 | 2.88E−03 | 4.46E−03 |
| 30 | 2629 | Stomach |  | 2196 |  | 5.30E−01 |
|  | 151297 | Sm Intes |  | 150864 |  | 3.64E+01 |
|  | 2229 | Lg Intes |  | 1796 |  | 4.33E−01 |
|  | 116731 | Urine |  | 116298 |  | 2.81E+01 |
|  | 901 | Urine |  | 468 |  | 1.13E−01 |
|  | 423 | Urine |  | 10 |  | 0.00E+00 |
|  | 424 | BKG |  | 10 |  |  |

BKG AVG = 434

TABLE III

TIME: 30 Minute Biodistribution
DATE: 8/6/91  LIGAND: DOTPMB-K,  METAL: Gd-159,  COMMENTS: 99% Complexation
4:1, LIG:MET Molar Ratio, (Metal = 3 × 10-4M)

|  | % DOSE/GRAM RAT 3 |
|---|---|
| WEIGHT: 235.14 | |
| Bone | 0.006 |
| Tail | 0.013 |
| Liver | 0.016 |
| Kidney | 0.121 |
| Spleen | 0.000 |
| Muscle | 0.000 |
| Blood | 0.000 |
| Heart | 0.000 |
| Lung | 0.009 |
| Brain | 0.004 |
| 0.000 = No Activity Detected | |
| Bone | 0.109 |
| Tail | 0.038 |
| Liver | 0.196 |
| Kidney | 0.303 |
| Spleen | 0.000 |
| Muscle | 0.026 |
| Blood | 0.000 |
| Heart | 0.000 |
| Lung | 0.012 |
| Brain | 0.005 |
| Stomach | 0.012 |
| Sm Intes | 51.549 |
| Lg Intes | 2.232 |

TABLE V

One Hour Biodistribution, Imaged Rat

TIME: One Hour biodistribution
DATE: 8/8/91  LIGAND: DOTPMB-K, D.  METAL: Sm = 153  COMMENTS: 99% Complex
4:1, LIG:MET Molar Ratio (Metal = 3 × 10-4M)

|  | % DOSE/GRAM | % DOSE |
|---|---|---|
| WEIGHT: 263.82 | | |
| Bone | 0.004 | 0.067 |
| Tail | 0.038 | 0.093 |
| Liver | 0.014 | 0.144 |
| Kidney | 0.084 | 0.245 |
| Spleen | 0.016 | 0.011 |
| Muscle | 0.001 | 0.078 |
| Blood | 0.001 | 0.019 |
| Stomach | | 45.144 |
| Smll Int | | 31.408 |
| Lrg Int | | 0.003 |

TABLE IV (see legend for Table III)

| DATA | COUNTS | ORGAN | N ENTER WT | BCKG COR | % DOSE/G | % DOSE |
|---|---|---|---|---|---|---|
| 1 | | Std A | × Rat 1 Wt | 0 | | |
| 1 | | Std B | × 235.14 | 0 | | |
| 2 | 414367 | Std C | av 413946 | 413946 | | |
| 3 | 439 | Bone | 0.69 | 18 | 6.30E-03 | 1.09E.01 |
| 4 | 578 | Tail | 2.95 | 157 | 1.29E-02 | 3.79E-02 |
| 5 | 1232 | Liver | 11.96 | 811 | 1.64E-02 | 1.96E-01 |
| 6 | 1675 | Kidney | 2.51 | 1254 | 1.21E-01 | 3.03E-01 |
| 7 | 418 | Spleen | 0.66 | 0 | 0.00E+00 | 0.00E+00 |
| 8 | 423 | Muscle | 1.91 | 2 | 2.53E-04 | 2.56E-02 |
| 9 | 412 | Blood | 1.84 | 0 | 0.00E+00 | 0.00E+00 |
| 10 | 417 | Heart | 0.85 | 0 | 0.00E+00 | 0.00E+00 |
| 11 | 470 | Lung | 1.25 | 49 | 9.47E-03 | 1.18E-02 |
| 12 | 442 | Brain | 1.28 | 21 | 3.96E-03 | 5.07E-03 |
| 13 | 470 | Stomach | | 49 | 1.18E-02 | |
| 14 | 213806 | Sm Intes | | 213385 | | 5.15E+01 |
| 15 | 9661 | Lg Intes | | 9240 | | 2.23E+00 |
| 16 | 102818 | Urine | | 102397 | | 2.47E+01 |
| 17 | 12520 | Urine | | 12099 | | 2.92E+00 |
| 18 | 1447 | Urine | | 26 | | 6.28E-03 |
| 19 | 1421 | BKG | | | | |

BKG AVG = 421

TABLE VI

24 Hour Biodistribution, Imaged Rat

TIME: 24 Hour biodistribution
| DATE | LIGAND | METAL | COMMENTS |
|---|---|---|---|
| 8/8/91 | DOTPMB-K | Sm = 153 | 99% Complex |

4:1, LIG:MET Molar Ratio (Metal = $3 \times 10^{-4}$M)

| | % DOSE/GRAM | % DOSE |
|---|---|---|
| WEIGHT: 163.82 | | |
| Bone | 0.008 | 0.146 |
| Tail | 0.015 | 0.036 |
| Liver | 0.010 | 0.106 |
| Kidney | 0.154 | 0.451 |
| Spleen | 0.029 | 0.020 |
| Muscle | 0.017 | 1.883 |
| Blood | 0.000 | 0.004 |
| Stomach | | 0.053 |
| Smll Int | | 2.109 |
| Smll Int | | 19.611 |
| Lrg Int | | 8.351 |
| Feces | | 35.981 |
| Urine | | 2.799 |
| Paper | | 0.126 |

TABLE VII

Rat Injected: 8/8/91

TIME: 72 hour biodistribution
| Date: | Ligand | Metal | Comments |
|---|---|---|---|
| 8/12/91 | DOTPMB-K | Sm-153 | 99% Complex |

4:1, LIG:MET MOLAR RATIO (Metal = $3 \times 10^{-4}$M)

| | % DOSE/GRAM | % DOSE |
|---|---|---|
| WEIGHT: 269.58 | | |
| Bone | 0.014 | 0.219 |
| Tail | 0.002 | 0.005 |
| Liver | 0.002 | 0.030 |
| Kidney | 0.019 | 0.054 |
| Spleen | 0.000 | 0.000 |
| Muscle | 0.000 | 0.000 |
| Blood | 0.000 | 0.000 |
| Feces | | 5.832 |
| Feces | | 5.467 |
| Feces | | 2.464 |
| Urine | | 0.077 |
| Bladder | | 0.242 |

TABLE VIII

File = BTY15ST Summary Standardized Data Mouse #2
(15 minute biodistribution), 99% complex, 25.0 UL dose
Ca added to complex at 1;1 molar, lig: Ca

| DATE | LIGAND | METAL | COMMENTS |
|---|---|---|---|
| 10/30/91 | DOTPME-K | Sm-153 | #08-07-91 |

2:1, Lig:Met Molar Ratio (Metal = $3 \times 10^{-4}$M), pH 7 -= 8

% DOSE/GRAM

| | MOUSE 1 | MOUSE 2 | AVERAGE |
|---|---|---|---|
| WEIGHT | 15.854 | 10.702 | 13.278 |
| BONE | 0.171 | 3.169 | 1.670 |
| TAIL | 1.374 | 83.296 | 42.335 |
| LIVER | 3.979 | 66.441 | 35.210 |
| KIDNEY | 0.889 | 14.568 | 7.728 |
| SPLEEN | 1.260 | 0.831 | 1.046 |
| MUSCLE | 0.173 | 1.437 | 0.805 |
| BLOOD | 43.105 | 3.743 | 23.424 |
| HEART | 0.472 | 2.418 | 1.445 |
| LUNG | 0.697 | 2.735 | 1.716 |

TABLE VIII-continued

File = BTY15ST Summary Standardized Data Mouse #2
(15 minute biodistribution), 99% complex, 25.0 UL dose
Ca added to complex at 1;1 molar, lig: Ca

| DATE | LIGAND | METAL | COMMENTS |
|---|---|---|---|
| 10/30/91 | DOTPME-K | Sm-153 | #08-07-91 |
| BRAIN | 0.023 | 0.139 | 0.081 |
| TUMOR | 0.648 | 4.844 | 2.746 |
| STOMACH | 14.272 | 4.343 | 9.308 |
| SMALL INT. | 88.504 | 40.343 | 64.423 |
| LARGE INT. | 3.320 | 2.298 | 2.809 |
| URINE | 0.000 | 0.000 | 0.000 |
| BODY 1 | 0.408 | 1.637 | 1.022 |
| BODY 2 | 0.148 | 5.594 | 2.871 |

*MOUSE 2 DID NOT BECOME ACTIVE AFTER ANESTHESIA, HOWEVER ALIVE***

TABLE IX

| | % DOSE | |
|---|---|---|
| | MOUSE 1 | MOUSE 2 |
| BONE | 0.149 | 2.100 |
| LIVER | 3.379 | 37.732 |
| KIDNEY | 0.199 | 3.610 |
| SPLEEN | 0.095 | 0.039 |
| MUSCLE | 1.179 | 6.615 |
| BLOOD | 44.420 | 2.604 |
| HEART | 0.033 | 0.157 |
| LUNG | 0.090 | 0.210 |
| BRAIN | 0.010 | 0.054 |
| TUMOR | 0.062 | 0.237 |
| STOMACH | 3.565 | 0.586 |
| SMALL INT. | 86.734 | 27.837 |
| LARGE INT. | 2.994 | 1.145 |
| URINE | 12.857 | 0.007 |
| BODY 1 | 2.294 | 6.890 |
| BODY 2 | 0.585 | 17.147 |

Changes may be made in the construction, operation and arrangement of the various parts, elements, steps and procedures described herein without departing from the concept and scope of the invention as defined in the following claims.

What is claimed is:

1. A polyazamacrocyclic compound or a salt thereof, the compound having the formula

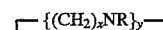

where x is 2, 3 or a combination of p 2(s) and q 3(s) where p+q=y;

y is 3 or 4;

R is $(CH_2)_zP(=O)OR^1OR^2$;

$R^1$ is H or $CH_3$;

$R^2$ is $C_nH_{1+2n}$;

z is 1 to 3; and n is 4 to 6.

2. A polyazamacrocyclic compound-metal complex having the formula

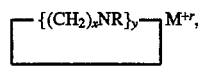

where x is 2, 3 or a combination of p 2(s) and q 3(s) where p+q=y;

y is 3 or 4;

R is $(CH_2)_zP(=O)OR^1OR^2$;

$R^1$ is H or $CH_3$;

$R^2$ is $C_nH_{1+2n}$;

z is 1 to 3;

r is 2 or 3;

M is a metal ion; and n is 4 to 6.

3. The compound of claim 1 where y is 3.
4. The compound of claim 1 where y is 4.
5. The compound of claim 1 where y is 3 and x is 2.
6. The compound of claim 1 where y is 4 and x is 2.
7. The complex of claim 2 where y is 3.
8. The complex of claim 2 where y is 4.
9. The complex of claim 2 where y is 3 and x is 2.
10. The complex of claim 2 where y is 4 and x is 2.
11. The compound of claim 1 where y is 3, p is 1 and q is 2 or p is 2 and q is 1.
12. The complex of claim 2 where y is 3, p is 1 and q is 2 or p is 2 and q is 1.
13. The compound of claim 1 where y is 4, p is 1 and q is 3, p is 2 and q is 2 or p is 3 and q is 1.
14. The complex of claim 2 where y is 4, p is 1 and q is 3, p is 2 and q is 2 or p is 3 and q is 1.
15. The compound of claim 1 where z is 1.
16. The complex of claim 2 where z is 1.
17. The compound of claim 1 where $R^2$ is $C_4H_9$.
18. The complex of claim 2 where $R^2$ is $C_4H_9$.
19. The complex of claim 2 where M is a lanthanide element.
20. The complex of claim 2 where $M^{+r}$ is $Gd^{+3}$.
21. A compound or salt thereof, the compound having the formula:

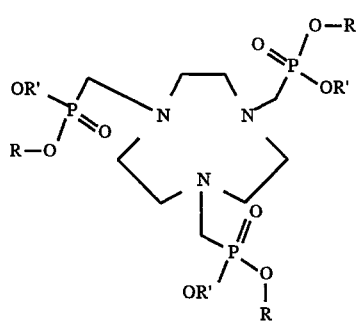

where

R is $C_nH_{1+2n}$;

n is 4 to 6; and

R' is H.

22. A compound or salt thereof, the compound having the formula:

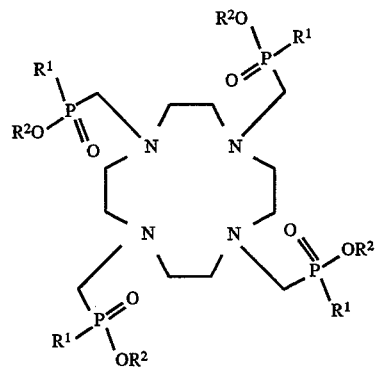

where $R^1$ is $OC_nH_{1+2n}$;

n is 4 to 6; and $R^2$ is H.

23. The compound of claim 21 or 22 where n is 4.

24. A polyazamacrocyclic compound or a salt thereof, the compound having the formula

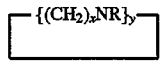

where x is 2, 3 or a combination of p 2(s) and q 3(s) where p+q=Y;

y is 3 or 4

R is $(CH_2)_zP(=O)OR^1OR^2$;

$R^1$ is H;

$R^2$ is $C_4H_9$; and z is 1 to 3.

25. A polyazamacrocyclic compound-metal complex having the formula

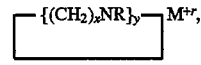

where x is 2, 3 or a combination of p 2(s) and q 3 (s) where p+q=y;

y is 3 or 4;
R is $(CH_2)_zP(=O)OR^1OR^2$;
$R^1$ is H;
$R^2$ is $C_4H_9$;
z is 1 to 3;
r is 2 or 3; and
M is a metal ion.
26. The complex of claim 25 where $M^{+r}$ is $Gd^{+3}$.
27. A compound or salt thereof, the compound having the formula:
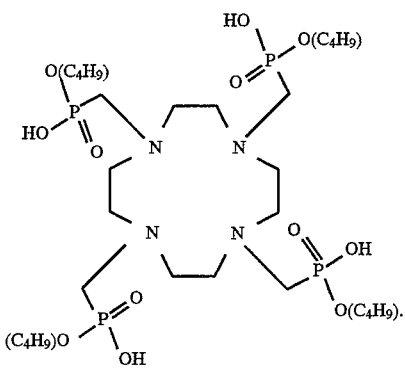
* * * * *